US012661367B2

(12) United States Patent
Huang et al.

(10) Patent No.: US 12,661,367 B2
(45) Date of Patent: Jun. 23, 2026

(54) ***STREPTOMYCES SPORORAVEUS* STRAIN AND A NEW ANTIBIOTICS AGAINST BACTERIA AND FUNGI**

(71) Applicant: National Taipei University of Technology, Taipei (TW)

(72) Inventors: Chih-Hung Huang, Taipei (TW); Pu-Chieh Chang, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 532 days.

(21) Appl. No.: 18/319,312

(22) Filed: May 17, 2023

(65) Prior Publication Data

US 2023/0405036 A1    Dec. 21, 2023

Related U.S. Application Data

(60) Provisional application No. 63/343,298, filed on May 18, 2022.

(51) Int. Cl.
| | |
|---|---|
| *A61K 39/02* | (2006.01) |
| *A61K 31/7048* | (2006.01) |
| *A61P 31/04* | (2006.01) |
| *C12N 1/205* | (2026.01) |
| *C12R 1/465* | (2006.01) |

(52) U.S. Cl.
CPC .......... *A61K 31/7048* (2013.01); *A61P 31/04* (2018.01); *C12N 1/205* (2021.05); *C12R 2001/465* (2021.05)

(58) Field of Classification Search
CPC combination set(s) only.
See application file for complete search history.

(56) References Cited

PUBLICATIONS

Al-Askar et al (African Journal of Agricultural Research vol. 6(12), pp. 2835-2842, Jun. 18, 2011).*
Chang et al (Antibiotics. May 18, 2022. 11(5): 679, pp. 1-10).*

* cited by examiner

*Primary Examiner* — Jennifer E Graser
(74) *Attorney, Agent, or Firm* — Birch, Stewart, Kolasch & Birch, LLP

(57) ABSTRACT

Disclosed herein is a UV mutagenesis produced new *Streptomyces spororaveus* strain SC263 that exhibits an increased thermostability of the antibiotic produced, which shows antibiotic activity against bacteria and fungi. Also provided are the antibiotic produced by SC263 and a composition thereof for treatment of bacterial and fungal infections. The antibiotic has a very high molecular weight, which is suitable for topical administration.

19 Claims, 5 Drawing Sheets
Specification includes a Sequence Listing.

(A)                   (B)

(A)                   (B)

STREPTOMYCES SPORORAVEUS STRAIN AND A NEW ANTIBIOTICS AGAINST BACTERIA AND FUNGI

CROSS REFERENCE

This Non-provisional application claims the priority under 35 U.S.C. § 119(e) on US Patent Provisional Application No. 63/343,298 filed on May 18, 2022, the entire contents of which are hereby incorporated by reference.

REFERENCE TO AN ELECTRONIC SEQUENCE LISTING

The application contains a Sequence Listing which has been submitted electronically in .XML format and is hereby incorporated by reference in its entirety. Said .XML copy, created on May 15, 2023, is named "HJH0002US-Sequence-Listing.xml" and is 8,221,249 bytes in size. The sequence listing contained in this .XML file is part of the specification and is hereby incorporated by reference herein in its entirety.

FIELD OF THE INVENTION

The present invention provides a new *Streptomyces spororaveus* strain SC263 and antibiotics produced by the strain SC263. The present invention also provides a composition containing the antibiotics against bacteria and fungi.

BACKGROUND OF THE INVENTION

Development of antimicrobial resistance in pathogenic bacteria and fungi has led to global health emergencies [1]. Annual death resulting from diseases caused by drug-resistant pathogens is estimated to be over 700,000 in more than 120 countries according to World Health Organization [2]. The urge for new antibiotics or antifungal compounds from natural products is eminent.

Patients with immunosuppression are prone to be infected with multi-drug resistance *Candida* [3] and *Aspergillus* [4]. Nearly all Clinical antifungal drugs exhibit a molecular weight lower than 2000 Da [5]. These commonly used drugs for antifungal infections including amphotericin B (used for intravenous injections), flucytosine (used for oral and intravenous injections), and itraconazole (used for oral and intravenous injections) may exhibit severe side effects such as nephrotoxicity, hepatoxicity, bone marrow suppression, and heart failure, limiting the use of these drugs [6-8]. Drug with less toxicity such as natamycin produced from *Streptomyces* species is considered relatively safe and for topical application such as eyedrops but is nearly insoluble in water with low bioavailability when orally used [9].

*Streptomyces* species, which are ubiquitous in fertile soil, are the major producers of natural products. They produce nearly 8,000 natural products, accounting for approximately 45% of all from the microbial sources [10]. About ⅔ of clinically useful antibiotics are produced by *Streptomyces* [11], including many important drugs, such as streptomycin, neomycin, kanamycin, rapamycin, chloramphenicol, vancomycin, etc. [12]. This genus is predicted to possess a repertoire of approximately 100,000 antibiotics, of which only 3% has been discovered [13]. For decades *Streptomyces* have been continuously explored for novel and useful antibiotics [14,15].

It is desirable to develop a new strain which can produce antibiotics with enhanced antibiotic efficacy.

BRIEF SUMMARY OF THE INVENTION

Disclosed herein is a new *Streptomyces spororaveus* strain SC263 that exhibited increased thermostability of the antibiotic peptide as produced.

The present invention also provides the antibiotic produced therefrom, named AF1, which shows antibiotic activity against at least six fungi and two Gram-positive bacteria, and exhibits an apparent molecular weight larger than 5 kDa, particularly larger than 100 kDa, which is unusual in antibiotics. Also disclosed herein is the use of AF1, especially for manufacturing an antifungal composition.

In one aspect, the present invention provides a new *Streptomyces spororaveus* strain SC263 producing antibiotics with increased thermostability.

In the present invention, the *Streptomyces spororaveus* strain SC263 was deposited on May 30, 2022 at Leibniz-Institut, Deutsche Sammlung von Mikroorganismen und Zellkulturen GmbH (DSMZ) in Germany, at Inhoffenstr. 7B, D-38124 Braunschweig, Germany, which is an International Depositary Authority (IDA) under Budapest Treaty in World Intellectual Property Organization. The accession number is DSM 34277.

In one embodiment of the present invention, the strain SC263 has the DNA sequence set forth in SEQ ID NO.: 1

In another embodiment of the present invention, the strain SC263 has the DNA sequence set forth in SEQ ID NO.: 2.

In one further embodiment of the present invention, the strain SC263 has the DNA sequence set forth in SEQ ID NO.: 3.

In one further aspect, the present invention provides a composition comprising the strain SC263.

In one yet aspect, the present invention provides an antibiotic AF1, which is produced by the strain SC263, and exhibits an apparent molecular weight of larger than 5 kDa, particularly larger than 100 kDa, measured by membrane-filtration concentration.

In one embodiment of the present invention, the composition comprises an antibiotic exhibiting an apparent molecular weight of larger than 100 kDa, and an antibiotic exhibiting an apparent molecular weight of 10 kDa to 100 kDa, measured by membrane-filtration concentration.

In one embodiment of the invention, the antibiotic AF1 is effective against fungi.

In one embodiment of the invention, the antibiotic AF1 is effective against Gram-positive bacteria.

In yet another aspect, the present invention provides an antimicrobial composition comprising the antibiotic produced by *Streptomyces spororaveus* strain SC263, and a pharmaceutically acceptable carrier.

In one embodiment of the invention, the composition is for treatment of a fungal infection.

In one embodiment of the invention, the composition is for treatment of a bacterial infection, particularly a Gram-positive bacterial infection.

In one embodiment of the invention, the composition is administered topically.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
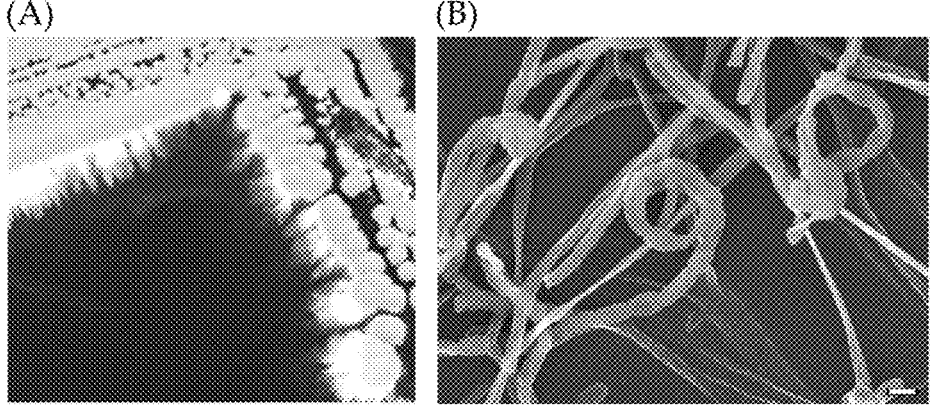
FIG. 1 shows the morphology of SC26: (A) Colony morphology of SC26 on YM1 agar after incubation at 30° C. for 6 days. (B) Spore chains of SC26 under field-emission scanning electron microscope (FE-SEM). The bar indicates 1 μm.

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The term "composition" as used herein, refers a product that results from the mixing or combining of more than one active ingredient and includes both fixed and non-fixed combinations of the active ingredients. The term "fixed combination" means that the active ingredients and a certain co-agent are both administered to a patient simultaneously in the form of a single entity or dosage. The term "non-fixed combination" means that the active ingredients and a certain co-agent are administered to a patient as separate entities either simultaneously, concurrently or sequentially with no specific intervening time limits, wherein such administration provides effective levels of the two agents in the body of the patient. The latter also applies to cocktail therapy, e.g., the administration of three or more active ingredients.

The term "composition" or "pharmaceutical composition" used herein refers to a therapeutically effective amount of the antibiotic produced by SC263 and optionally a pharmaceutically acceptable carrier.

The term "pharmaceutically acceptable" used herein refers to the situation in which within the scope of reasonable medical judgment, a drug is suitable for use in contact with a tissue of a subject (such as a human) taking the drug, without excessive toxicity, irritation, allergic reaction, or other problems or complications, and with reasonable benefit/risk ratio. Each carrier must be compatible with other ingredients in order to be "acceptable".

The term "carrier" used herein refers to a non-toxic compound or agent that has the function of assisting cells or tissues to absorb active ingredient. The carrier is selected from, for example, excipients, adjuvants, diluents, fillers, or bulking agents, granulating agents, coating agents, release control agents, binding agents, disintegrants, lubricants, preservatives, surfactants, antioxidants, buffers, suspending agents, thickeners, stabilizers, or other carriers used in pharmaceutical compositions. Examples of carriers include, but are not limited to, polyvinyl alcohol, povidone, hydroxy-propyl methyl cellulose, poloxamers, hydroxyethyl cellulose cyclodextrin, carboxymethylcellulose (CMC), phosphate buffered saline (PBS), water, emulsifier (such as oil and water emulsifier), or wetting agent. Tonicity adjustors may be added as needed or convenient. They include, but are not limited to, salts, particularly sodium chloride, potassium chloride, mannitol and glycerin, or any other suitable tonicity adjustor. Various buffers and means for adjusting pH may be used so long as the resulting preparation is acceptable.

<table>
</table>

5

Accordingly, buffers include acetate buffers, citrate buffers, phosphate buffers and borate buffers. Acids or bases may be used to adjust the pH of these formulations as needed. Similarly, an acceptable antioxidant for use in the present disclosure includes, but is not limited to, sodium metabisulfite, sodium thiosulfate, acetylcysteine, butylated hydroxyanisole and butylated hydroxytoluene. Other excipient components which may be included in the preparations are chelating agents. The preferred chelating agent is edetate disodium, although other chelating agents may also be used in place of or in conjunction with it.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a peptide or protein as disclosed herein required to provide a clinically significant decrease in disease symptoms. An appropriate "effective" amount in any individual case may be determined using techniques, such as a dose escalation study.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

In the invention, *Streptomyces* strain SC26 was obtained by an isolation from the mountain region in northern Taiwan, and then a late-sporulating mutant was obtained from the culture of the strain SC26, which was named as SC263. It was unexpectedly found that the strain SC263 can produce an antibiotic exhibiting much higher thermostability than the antibiotic produced by the strain SC26. The genomic sequence of SC263 was determined, which was classified to a known species *Streptomyces spororaveus* by a pairwise comparison between SC263 and *S. spororaveus* NBRC15456. According to sequencing results, the genome of SC263 contains the DNA sequence of SEQ ID NO: 1, the DNA sequence of SEQ NO: 2, or the DNA sequence of SEQ ID NO: 3.

The present invention provides a new *Streptomyces spororaveus* strain SC263 producing antibiotic with increased thermostability.

The present invention also provides a composition comprising the strain SC263 or the antibiotic produced by the strain SC263. In the composition, the strain SC263 is viable or inactivated.

According to the invention, the antibiotic produced by the strain SC263 exhibits an apparent molecular weight of larger than 100 kDa by membrane-filtration concentration.

In one example, the antibiotic is used for preparing an antimicrobial composition against bacteria or fungi.

In one embodiment, the composition is a pharmaceutical composition, which may be administered topically to a subject's skin.

The present invention is further illustrated by the following examples, which are provided for the purpose of demonstration rather than limitation.

6

Materials and Methods

Soil Sample Collection and Isolation of SC26

Soil samples were collected from the mountains in northern Taiwan and stored in sterile bags at 4° C. until use. The samples were sieved through 1-mm metal mesh, suspended in sterile water, serially diluted, plated on YM1 agar (0.4% Yeast extract, 1% malt extract), and incubated at 30° C. for 5 to 7 days. Individual colonies that produced spores were picked and streaked onto YM1 agar. Spores from these isolates were collected, suspended in sterile 20% glycerol, and stored at −80° C.

Morphology Under Electron Microscope

Spore chains of SC263 were collected from a 5-day culture growing on a cover slide on YM1 agar, fixed with liquid nitrogen, coated with gold particle, and observed under a Thermal Field Emission Scanning Electron Microscope (FE-SEM) JSM-7610F (JOEL Ltd., Tokyo, Japan).

Phylogenetic Analysis of 16S rRNA

Full-length 16S rRNA sequences was amplified by PCR using primers 27F and reverse primer 1492R and subjected to Sanger sequencing. The 16S rRNA sequence of SC263 was compared to the database on BLASTN web server at National Center for Biotechnology Information (NCBI). Sixty-two top hit sequences were ported to MEGA11 for alignment and phylogenetic tree construction [27,28].

Microbial Strains and Culture Conditions

The fungi used in antibiotic tests were *Aspergillus niger* ATCC 16878, *Aspergillus brasiliensis* ATCC 16404, *Candida albicans* ATCC 10231, *Candida tropicalis* ATCC 13803, *Nannizzia gypsea* ATCC 14683, and *Saccharomyces cerevisiae* BCRC 22286. Two Gram-positive bacterial used were *Bacillus subtilis* ATCC 6051 and *Staphylococcus aureus* ATCC 6538. Three Gram-negative bacteria used were *Escherichia coli* ATCC 8739, *Salmonella Typhimurium* SL1344, and *Salmonella Enteritidis* ATCC 13076.

Information of the further tested yeasts/fungi is provided in Table M below.

TABLE M

| | Further tested yeasts/fungi | | | |
|---|---|---|---|---|
| | Yeast/fungus | ATCC | BCRC | Note |
| 1 | *Aspergillus brasiliensis* | 16404 | 30506 | Mycotoxin |
| 2 | *Aspergillus flavus* | 9643 | 30144 | Most common *Aspergillus* infection |
| 3 | *Aspergillus niger* | 16878 | 32214 | Mycotoxin |
| 4 | *Candida albicans* | 10231 | 21538 | Multidrug-resistant |
| 5 | *Candida glabrata* | 2001 | 20586 | Multidrug-resistant |
| 6 | *Candida krusei* | 2143 | 23171 | Multidrug-resistant |
| 7 | *Candida tropicalis* | 13803 | 20521 | Multidrug-resistant |
| 8 | *Epidermophyton floccosum* | 18397 | 30531 | Skin and nail infection |
| 9 | *Hortaea werneckii* | | FU30545 | Epidermomycosis, ringworm |
| 10 | *Komagataella phaffii* | Strain: KM71H | | |
| 11 | *Microsporum canis* | 36299 | 30541 | Hong Kong feet/ringworm |
| 12 | *Nannizzia gypsea* | 14683 | 30542 | |
| 13 | *Saccharomyces cerevisiae* | | 22286 | |
| 14 | *Trichophyton mentagrophytes* | 9533 | 32066 | Multidrug-resistant |
| 15 | *Trichophyton rubrum* | 10218 | 32805 | Dermatophytes |
| 16 | *Trichosporon inkin* | | 21503 | Infection after surgery |
| 17 | *yarrowia lipolytica* | Strain: PO1g | | |

Further tested Gram-positive bacteria include *Bacillus subtilis* ATCC 6051 and *Staphylococcus aureus* ATCC 6538.

The test fungi were propagated on Sabouraud dextrose agar (SDA). The test bacteria were propagated tryptone soy agar (TSA). All bacteria and fungi were incubated at 30° C.

*Streptomyces* was cultured on solid YM1 agar and incubated at 30° C., or shaken in liquid YM1 broth at 30° C.

Cross Streak Screening for Antibiotic Activity

Actinomycete-like soil isolates were streaked on YM1 agar and incubated for 24 hours at 30° C. One microliter of the test bacteria or fungi containing $10^3$ colony-formation-unit (CFU) was spotted perpendicularly (FIG. 5A), and incubation was continued for four more days [29].

Zone of Inhibition Assays for Antibiotic Activities

All inoculants containing $10^5$ CFU each (except for *A. brasiliensis, A. niger*, and *N. gypsea*, which contained $10^6$ each) were spread on YM1 agar. Ten 11.1 of liquid containing the antibiotic (AF1) was spotted. For culture supernatant, the culture was grown at 30° C. for 24 hours and centrifuged at 12000 g for 5 minutes. The supernatant was collected and used for inhibition assays. For lyophilized powder, 0.1 g was dissolved in 1 ml sterile water. The plates were incubated at 30° C. for 5 days.

Membrane-Filtration Concentration of SC263

10 kDa and 100 kDa Centrifugal Filter Unit (AMICON) were used to identify the molecular weight of AF1. Two liters of SC263 culture supernatant was filtered through a 100 kDa mPES membrane (#D04-100 kDa, Repligen-Spectrumlabs) until the volume was reduced to 500 ml. The filtrated and the retained fractions were tested for antibiotic activities.

UV Mutagenesis of SC26

UV mutagenesis of *Streptomyces* was performed according to Kumar [31]. The surviving colonies were streaked onto a new plate and selected for late sporulating mutants.

Treatment with Lytic Enzyme

For cultured supernatant or F100 of SC263, proteinase K and pronase E were added to a concentration of 0.04 mg/mL and incubated at 37° C. for an hour. RNaseA or DNaseI were treated at 1 mg/mL and incubated at 37° C. for 0.5 hour. Pancreatin (Sigma-Aldrich) from porcine pancreas which composed of amylase, trypsin, lipase, ribonuclease and protease was added at 10 mg/mL 37° C. for an hour.

Genomic DNA Purification

SC263 was grown in YM1 at 30° C. for 3 days. The mycelia were harvested by centrifugation and washed in 10% sucrose. Genomic DNA was extracted according to Kutchma et. al. [32]. Purified genomic DNA was stored in TE buffer (10 mM Tris-HCl, 0.1 mM EDTA, pH 8.0) at −20° C.

Whole-Genome Sequencing

Genomic DNA was processed according to the assay protocol of PacBio CLR. The sequencing format is SMRT-cell sequencing via Sequel IIe platform. The sequence reads were assembled using SMRT Link (version 10.1.0.119588). The resulting three contigs achieved a QV score at least 91.39. Contigs with a score lower than 90 were removed.

Genomic Analysis

Annotation of the SC263 genome was conducted using NCBI Prokaryotic Genome Annotation Pipeline (PGAP), and the results were deposited to NCBI database with an accession number of JAKGSF000000000. Average nucleotide identity (ANI) was conducted using OrthoANI [22]. Genome-wide similarity comparison was conducted using Easyfig [33]. The presence of biosynthetic gene clusters was mined using anti SMASH 6.0 [23].

Results

Example 1: Isolation of Antibiotic-Producing SC26

A total of six soil samples from the mountain areas in northern Taiwan were screened for microbes on YM1 agar. Among colonies grown from these samples, isolate SC26 showed actinomycetes-like morphology including grey spores (FIG. 1A). Under field-emission scanning electron microscope (FE-SEM) SC26 displayed mycelia and coiled spore chains (FIG. 1B), characteristic of *Streptomyces*.

Figure 2:
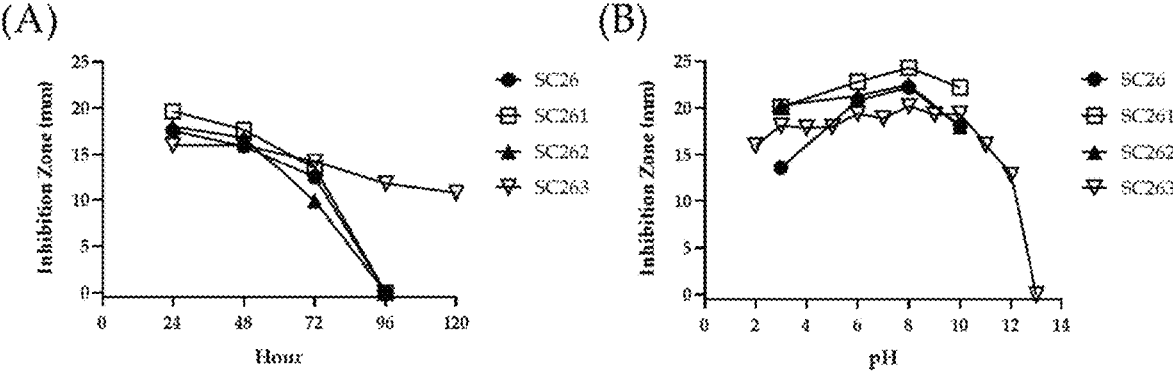
FIG. 2 shows the antifungal characteristics of SC26 and its derivatives. The antifungal activity of SC26 and its derivatives was examined using different fermentation hours until day 5 (A) and treated under different pH conditions from 24-hour cultured broth (B). All inhibition zones against *C. albicans* were measured.
Figure 3:
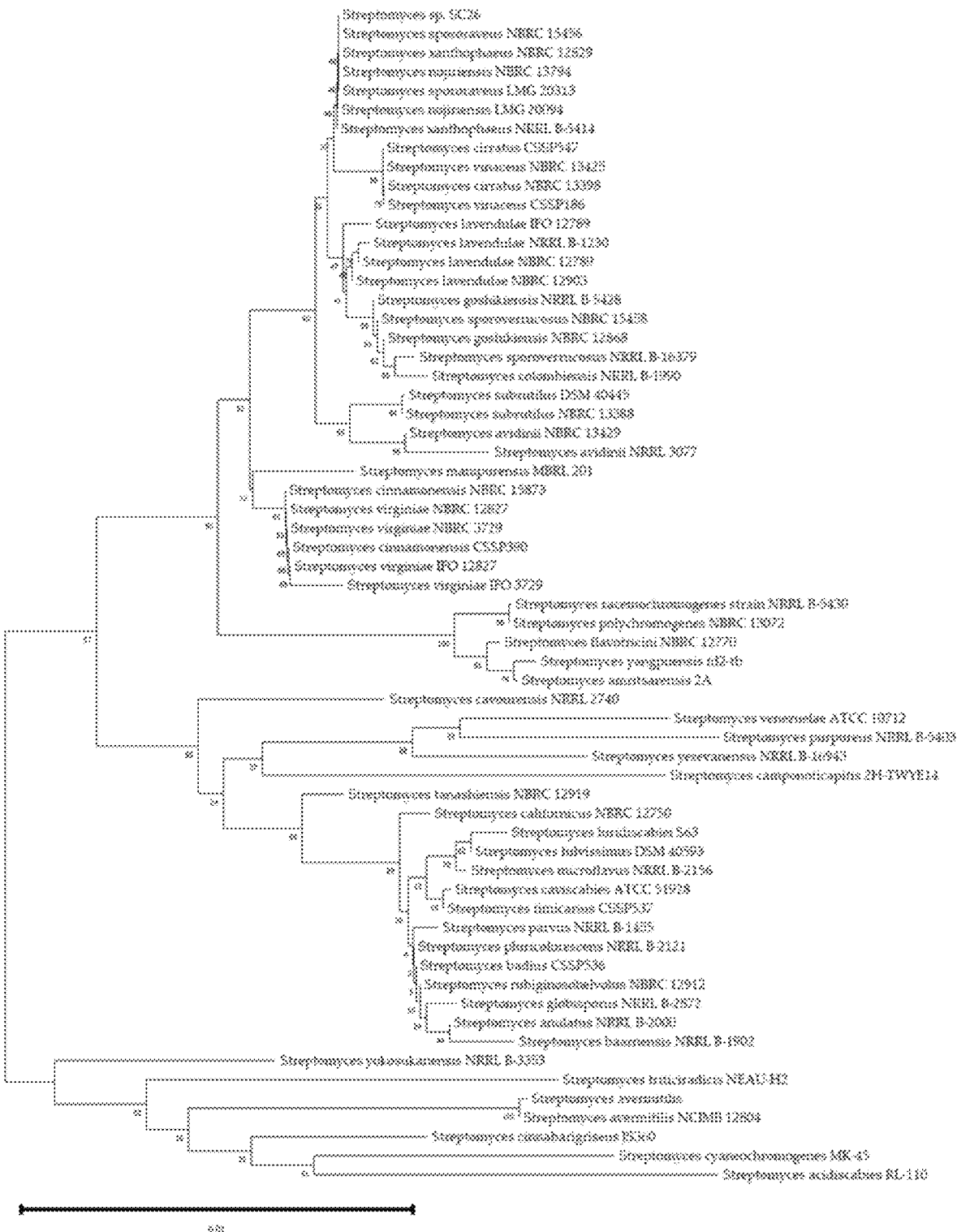
FIG. 3 shows a phylogenetic Tree of 16S ribosomal RNA of SC26. Maximum-likehood phylogenetic analysis was based on 16S rRNA gene sequences from 62 *Streptomyces*. The tree is drawn to scale, with branch lengths, indicating the number of substitutions per site between species using MEGA 11.

Culture supernatant of SC26 exhibited antibiotic activity against fungus *C. albicans* ATCC 10231 (FIG. 2A). The 16S rRNA sequence of SC26 was determined. Phylogenetic analysis showed that the SC26 16S rRNA was clustered into the same Glade as *Streptomyces spororaveus* NBRC 15456 and LMG 20313, *Streptomyces xanthophaeus* NBRC 12829 and NRRL B-5414, *Streptomyces nojiriensis* NBRC 13794 and LMG 20094 among 62 *Streptomyces* species compared (FIG. 3).

Example 2: Isolation and Characterization of UV-Mutagenesis Derivatives

The antibiotic produced by SC26 (designated AF1) was heat labile, destroyed in 3-5 hours at 65° C. (FIGS. 4A, 4B). UV mutagenesis of SC26 was conducted to search for strains producing relatively heat-stable AF1. Three mutant strains (SC261, SC262, and SC263) were chosen for their delayed sporulation (by 2 days compared to SC26). These mutants exhibited no difference in colony morphology and time course of AF1 production (FIG. 2A) from SC26.

Figure 4:
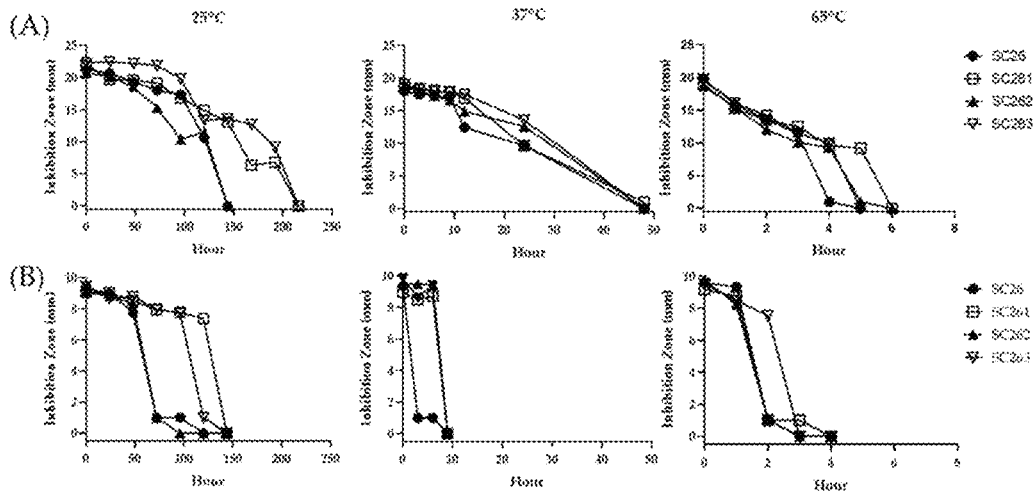
FIG. 4 shows the temperature stability of the bioactive compounds from SC26 and its derivatives. Overnight cultured broths from SC26 and its three derivatives (SC261, SC262 and SC263) were stored at 25° C., 37° C., and 65° C. Antimicrobial activity against *C. albicans* (A) and *S. aureus* (B) was measured at different time points.

Thermostability of AF1 produced by these mutants was conducted against *C. albicans* and *Staphylococcus aureus* ATCC 6538 (FIG. 4). AF1 produced by SC262 exhibited similar heat lability as that produced by SC26, whereas AF1 produced by SC261 and SC263 were stable for up to 192 hours at 25° C. against *C. albicans* and up to 144 hours against *S. aureus*. SC263 was chosen for further detailed studies.

Figure 5:
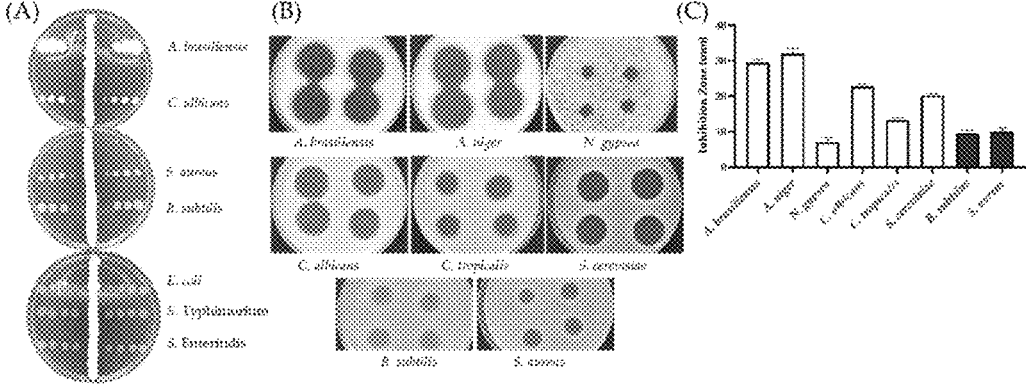
FIG. 5 shows the antibacterial and antifungal activities of SC263: (A) Antibiotic activity of SC263 using a cross-streak method for a 6-day incubation. An aliquot of 1 μL of bacterial suspension containing $10^3$ CFU were spotted cross the central line of SC263. (B) Ten-microliter of SC263 culture suspension was spotted in quadruplicates on lawns of test fungi and bacteria. *A. brasiliensis, A. niger*, and *N. gypsea*, was seeded with $10^6$ CFU each plate. The rest was seeded with $10^5$ CFU. (C) The diameters of inhibition zones were measured in triplicate. The error bars are calculated based on the quadruplicate zones for each tested microbe. White columns indicate fungi and black as Gram-positive bacteria.

A pH stability assay was conducted on AF1 of SC26 and its derivatives. AF1 of SC26 was relatively unstable at pH 3 and pH 10 compared with those by its derivatives (FIG. 5B). AF1 of SC263 was relatively stable from pH 2 to 12 but diminished at pH 13 to 14.

Example 3: Antimicrobial Activities of AF1 from SC263

AF1 of SC263 exhibited the same antibiotic spectrum as SC26, i.e., effective against two fungi (*Aspergillus brasiliensis* ATCC 16404 and *C. albicans*) and two gram-positive bacteria (*S. aureus* and *Bacillus subtilis* ATCC 6051), but not three Gram-negative bacteria (*Escherichia coli* ATCC 8739, *Salmonella Typhimurium* SL1344, and *Salmonella Enteritidis* ATCC 13076) (FIG. 5A).

In addition, AF1 of SC263 also inhibited four other fungi, *Aspergillus niger, Candida tropicalis, Nannizzia gypsea*, and *Saccharomyces cerevisiae* (FIG. 5C). The largest inhibition zone was found in *A. niger* with an average diameter of 32.0 mm, and the smallest was found in *N. gypsea* with 7.1 mm in diameter (FIG. 5C).

These inhibition zones produced by AF1 on the two Gram-positive bacteria were opaque (FIG. 5B), containing minute colonies which were able to grow when transfer to a new plate. In comparison, the inhibition zones in the fungal plates contained no viable cells. This suggests that the activity of AF1 against the two Gram-positive bacteria is bacteriostatic, not bactericidal.

Figure 9:
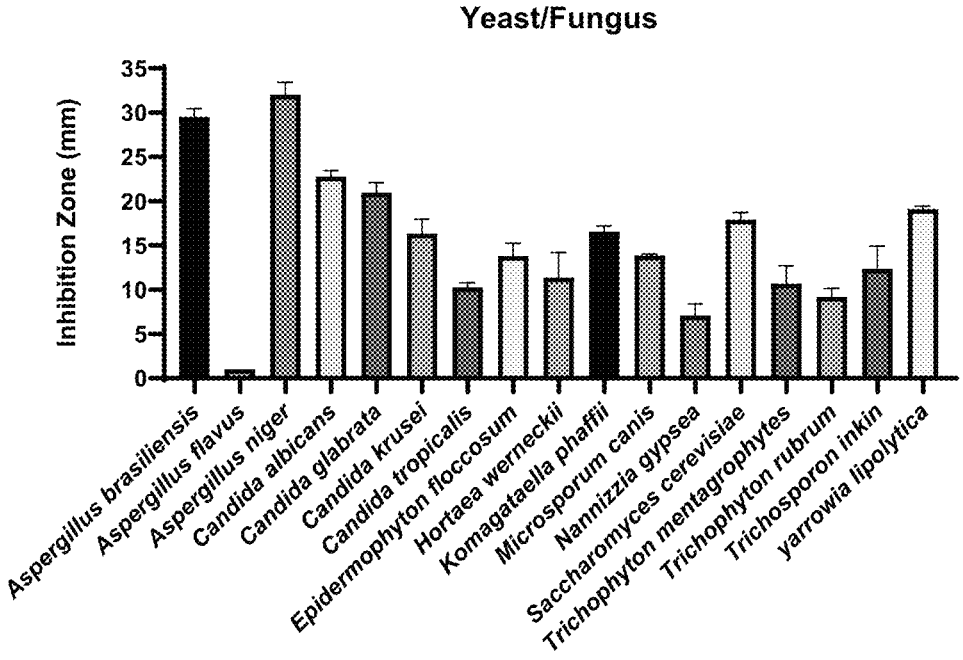
FIG. 9 shows the results of inhibition zone experiments for several yeasts/fungi.
Figure 10:
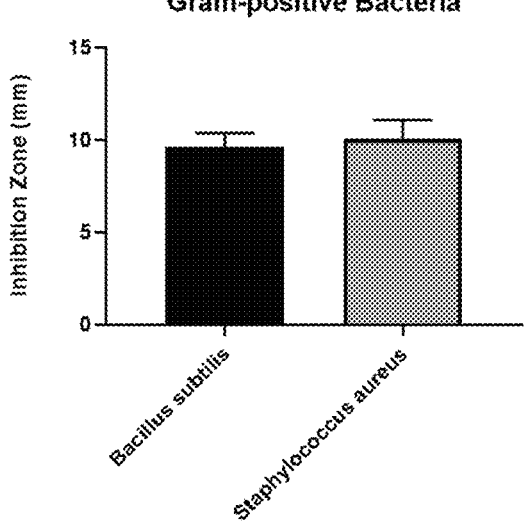
FIG. 10 shows the results of inhibition zone experiments for two Gram-positive bacteria.

Test results for more yeasts/fungi are shown in FIG. 9, and test results for two more Gram-positive bacteria are shown in FIG. 10.

Example 4: Characterization of the SC263 Antibiotics by Membrane-Filtration

Figure 6:
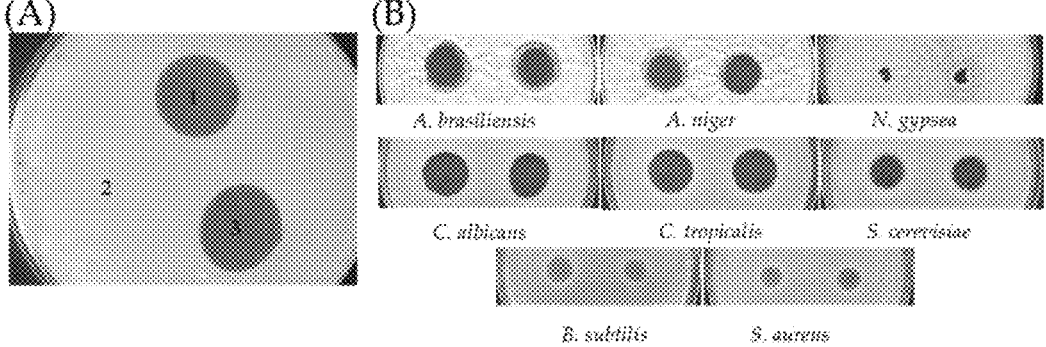
FIG. 6 shows the antibiotic activities of SC263 membrane filtrate. (A) Different fractions of SC263 cultured broth were tested against *C. albicans*. 1: culture broth; 2: filtrate<100 kDa; 3: compounds>100 kDa (F100 Fraction). (B) Reconstituted lyophilized powder was tested for zone of inhibition in duplicate spots against different fungi and Gram-positive bacteria.

To estimate the size of the AF1 in SC263, we filtered the cultured broths through a 10-kDa and a 100-kDa pore-size membrane. The active compound was absent in the filtrate, but present in the >100 kDa fraction (designated 'F100'; FIG. 6A). F100, when lyophilized and reconstituted, exhibited the same antibiotic spectrum as the culture supernatant (FIG. 6B).

The antibiotic in SC26 broth yielded the same sizing results. The large apparent size of AF1 distinguishes it from the majority of known antibiotics, which are mostly small metabolites [16]. Most known antifungal antibiotics are below the molecular weight of 2000 Da [5].

Figure 7:
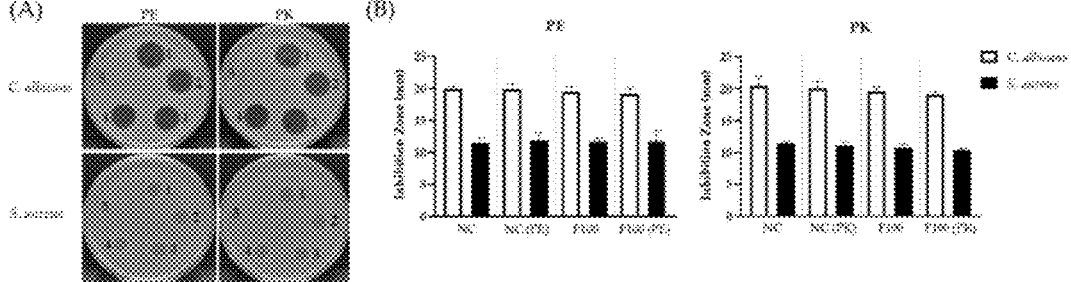
FIG. 7 shows the protease treatment of AF1 and F100 from SC263. (A) Antibiotic activities of AF1 and F100 individually treated with proteinase K (PK) or pronase E (PE) were examined. Numbers in this image indicate different treatment conditions as below. 1: AF1. 2: F100. 3: AF1 treated with PE or PK. 4: F100 treated with PE or PK. 5: PE or PK in sterile water. (B) The diameters of inhibition zones were measured.

Many large antifungal natural products are proteins [17, 18]. Treatment of the SC263 broth and F100 with either proteinase K or pronase E did not eliminate the antibiotic activity (FIG. 7), suggesting that the AF1 is not a protein. Treatment with DNaseI, RNaseA, or pancreatin (which composes of amylase, trypsin, lipase, ribonuclease, and protease) also did not extinguish the antibiotic activity of AF1 (data not shown).

Example 5: Genomic Sequence of SC263

To identify taxonomically SC263 and to investigate the secondary metabolic repertoire of SC263, whole genomic sequence of SC263 was determined. Three contigs, Ctg1 (7,201,269 bp), Ctg2 (996,243 bp), and Ctg3 (20,182 bp), were produced (Table 1). The overall GC content of 71.92%.

TABLE 1

| Genome Features of SC263 | |
| --- | --- |
| Feature | Characteristics |
| Number of Contigs | 3 |
| Total GC Content | 71.92% |
| Length (base pair, bp) | 8,217,694 |
| Ctg1 | 7,201,269 |
| Ctg2 | 996,243 |
| Ctg3 | 20,182 |
| Number of Genes | 7,370 |
| Number of RNAs | 91 |
| rRNA | 21 |
| tRNA | 73 |
| ncRNA | 3 |
| Number of Subsystems | 319 |
| Number of Pseudogenes | 197 |
| Number of BGCs | 28 (see Table 2) |

A total of 7,370 genes and 137 pseudogenes were annotated. Ninety-one RNAs, including 7 rRNAs, 73 tRNAs, and 3 non-coding RNAs were predicted. An origin of chromosome replication oriC was centrally located between dnaA and dnaN genes on Ctg1 (position 3,676,752-3,677,627) [19-21].

Four genomes in the same 16S rRNA Glade were used for pairwise comparison with SC263. The average nucleotide identity (ANI) values against *S. spororaveus* NBRC 15456, *S. nojiriensis* NBRC 13794, *S. xanthophaeus* NBRC 12829 and NRRL B-5414 were 99.57, 92.88, 86.57, 86.47, respectively. We therefore classified SC263 as *Streptomyces spororaveus*. Genome-wide comparison shows relatively high synteny between SC263 and NBRC 15456.

Example 5: Biosynthetic Gene Clusters in SC263

To assess the biosynthetic potential of secondary metabolites in SC263, we used antiSMASH webserver [23] to predict possible biosynthetic gene clusters (BGCs) on its genome. Ctg1 contained 21 predicted BGCs, Ctg2 contained 7, and Ctg3 contained none (Table 2). None of the predicted secondary metabolites produced by these BGC are larger than 2,000 Da.

TABLE 2

| | | | *S. spororaveus* SC263 | | *S. spororaveus* NBRC 15456 | |
| --- | --- | --- | --- | --- | --- | --- |
| BGC Type | Most similar known cluster | Notes | Region | Similarity | Region | Similarity |
| NRPS-like | lipstatin | NRP | 1-1 | 42% | 1 | 35% |
| T2PKS | spore pigment | Polyketide | 1-2 | 66% | 2 | 66% |
| NRPS, NRPS-like | JBIR-126 | NRP | 1-3 | 92% | 3 | 96% |
| NRPS, T1PKS | coelichelin | NRP | 1-4 | 72% | 4 | 72% |
| butyrolactone | neocarzinostatin | Polyketide: type I | 1-5 | 4% | 5 | 4% |
| NRPS, T1PKS | versipelostatin | Polyketide | 1-6 | 14% | 6 | 8% |
| siderophore | desferrioxamin B | Other | 1-7 | 100% | 7 | 100% |
| phenazine | lomofungin | Other | 1-8 | 34% | 8 | 34% |
| LAP | | | 1-9 | | 9 | |
| CDPS | BD-12 | NRP | — | — | 10 | 17% |
| siderophore | ficellomycin | NRP | 1-10 | 5% | 11 | 5% |
| T1PKS | ECO-02301 | Polyketide | 1-11 | 82% | 12 | 82% |
| NRPS-like | meoabyssomicin/ abyssomicin | Polyketide | 1-12 | 12% | — | — |
| NRPS-like, T2PKS | polyketomycin | Polyketide: type I + Type II | 1-13 | 39% | 13 | 41% |
| RiPP-like | | | 1-14 | | 14 | |
| terpene | toxoflavin/ fervenulin | Other | 1-15 | 14% | 15 | 14% |
| lanthipeptide-class-iv | | | 1-16 | | 16 | |

TABLE 2-continued

| | | | S. spororaveus SC263 | | S. spororaveus NBRC 15456 | |
|---|---|---|---|---|---|---|
| BGC Type | Most similar known cluster | Notes | Region | Similarity | Region | Similarity |
| NRPS | nogalamycin | Polyketide | 1-17 | 30% | 17 | 30% |
| terpene | hopene | Terpene | 1-18 | 61% | 18 | 61% |
| ectoine | ectoine | Other | 1-19 | 100% | — | — |
| lanthipeptide-class-I | | | 1-20 | | — | — |
| TIPKS, hglE-KS | saframycin A/ saframycin B | NRP | 1-21 | 4% | 19 | 4% |
| lanthipeptide-class-iii, terpene | SapB | RiPP:Lanthipeptide | 2-1 | 100% | 20 | 100% |
| terpene | 2-methylisoborneol | Terpene | 2-2 | 100% | 21 | 100% |
| terpene | monensin | Polyketide | 2-3 | 5% | 22 | 5% |
| melanin | melanin | Other | 2-4 | 28% | 23 | 28% |
| siderophore | | | 2-5 | | 24 | |
| T3PKS | alkylresorcinol | Polyketide | 2-6 | 100% | 25 | 100% |
| CDPS, NAPAA | | | 2-7 | | 26 | |

Figure 8:
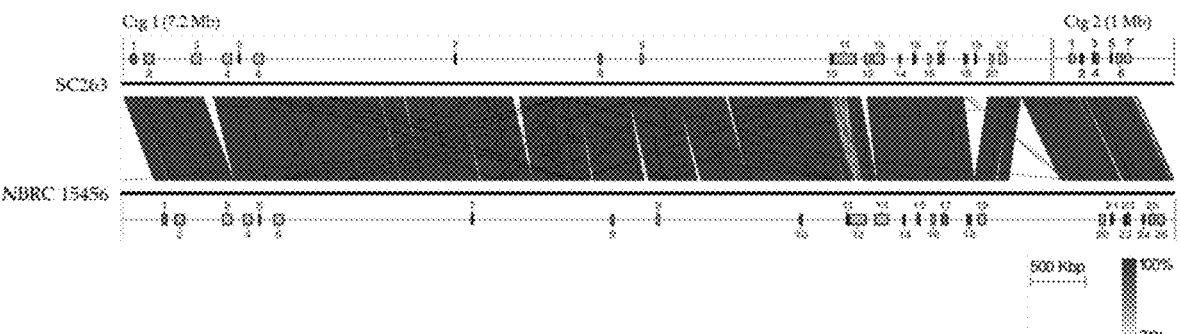
FIG. 8 shows the genome comparison between SC263 and *Streptomyces spororaveus* NBRC 15456. Biosynthetic gene clusters (BGCs) were predicted using anti SMASH 6.0 webserver and numbered by the order of these two strains in the top and bottom lines, respectively. Genome comparison between these two strains was generated using EASYFIG v. 2.2.5 and placed in the center.

The BGCs on the SC263 genome showed high similarity with those on the NBRC 15456 genomes (FIG. 8). Compared to the NBRC 15456 genome, the SC263 genome contained three additional BGCs: meoabyssomicin/abyssomicin (Region 1-12), ectoine (Region 1-19), and lanthipeptide-class-I (Region 1-20).

Interestingly, another closely related strain, *S. spororaveus* RDS28, which was isolated in Saudi Arabia, also exhibits an antifungal activity to many plant pathogens [24]. The nature of this antibiotic(s) is unknown.

In summary, *S. spororaveus* SC26 was isolated in northern Taiwan, which produces an antibiotic (AF1) against 6 fungi and 2 Gram-positive bacteria. From SC26, a mutant SC263 was isolated, which exhibited increase thermostability of AF1. AF1 produced by these strains is unusual in its apparent molecular weight, its dual antifungal and antibacterial activities. AF1 is a novel antibiotic which is resistant to proteolytic digestion.

The genomic sequences of SC263 contained 28 predicted BGCs, none of which appears to be involved in production of secondary metabolites larger than 2000 Da. Antibiotics with very high molecular weights are difficult to penetrate the skin barrier and are potentially safer for topical administration [34].

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

REFERENCES

1. Toner, E.; Adalj a, A.; Gronvall, G. K.; Cicero, A.; Inglesby, T. V. Antimicrobial resistance is a global health emergency. *Health Secur* 2015, 13, 153-155, doi:10.1089/hs.2014.0088.
2. Organization, W. H. *Global Action Plan on Antimicrobial Resistance;* 2015.
3. Healey, K. R.; Zhao, Y.; Perez, W. B.; Lockhart, S. R.; Sobel, J. D.; Farmakiotis, D.; Kontoyiannis, D. P.; Sanglard, D.; Taj-Aldeen, S. J.; Alexander, B. D.; et al. Prevalent mutator genotype identified in fungal pathogen *Candida glabrata* promotes multi-drug resistance. Nat Commun 2016, 7, 11128, doi:10.1038/ncomms11128.
4. Segal, B. H.; DeCarlo, E. S.; Kwon-Chung, K. J.; Malech, H. L.; Gallin, J. I.; Holland, S. M. *Aspergillus nidulans* infection in chronic granulomatous disease. *Medicine (Baltimore)* 1998, 77, 345-354, doi:10.1097/00005792-199809000-00004.
5. McKeny P T, N. T., Zito P M. Antifungal Antibiotics. 2021.
6. Ostrosky-Zeichner, L.; Rex, J. H.; Pappas, P. G.; Hamill, R. J.; Larsen, R. A.; Horowitz, H. W.; Powderly, W. G.; Hyslop, N.; Kauffman, C. A.; Cleary, J.; et al. Antifungal susceptibility survey of 2,000 bloodstream Candida isolates in the United States. *Antimicrob Agents Chemother* 2003, 47, 3149-3154, doi:10.1128/AAC.47.10.3149-3154.2003.
7. Mehrad, B.; Paciocco, G.; Martinez, F. J.; Ojo, T. C.; Iannettoni, M. D.; Lynch, J. P., 3rd. Spectrum of *Aspergillus* infection in lung transplant recipients: case series and review of the literature. *Chest* 2001, 119, 169-175, doi:10.1378/chest.119.1.169.
8. Eriksson, U.; Seifert, B.; Schaffner, A. Comparison of effects of amphotericin B deoxycholate infused over 4 or 24 hours: randomised controlled trial. *Bmj* 2001, 322, 579-582, doi:10.1136/bmj.322.7286.579.
9. Patil, A.; Lakhani, P.; Majumdar, S. Current perspectives on natamycin in ocular fungal infections. *Journal of Drug Delivery Science and Technology* 2017, 41, 206-212.
10. Chassagne, F.; Cabanac, G.; Hubert, G.; David, B.; Marti, G. The landscape of natural product diversity and their pharmacological relevance from a focus on the Dictionary of Natural Products®. *Phytochemistry Reviews* 2019, 18, 601-622, doi:10.1007/s11101-019-09606-2.
11. Hutchings, M. I.; Truman, A. W.; Wilkinson, B. Antibiotics: past, present and future. *Current Opinion in Microbiology* 2019, 51, 72-80.
12. de Lima Procopio, R. E.; da Silva, I. R.; Martins, M. K.; de Azevedo, J. L.; de Aranjo, J. M. Antibiotics produced by *Streptomyces. The Brazilian Journal of Infectious Diseases* 2012, 16, 466-471.
13. Watve, M. G.; Tickoo, R.; Jog, M. M.; Bhole, B. D. How many antibiotics are produced by the genus *Streptomyces? Arch Microbiol* 2001, 176, 386-390, doi:10.1007/s002030100345.

14. Nicault, M.; Tidjani, A.-R.; Gauthier, A.; Dumarcay, S.; Gelhaye, E.; Bontemps, C.; Leblond, P. Mining the Biosynthetic Potential for Specialized Metabolism of a *Streptomyces* Soil Community. *Antibiotics* 2020, 9, doi: 10.3390/antibiotics9050271.

15. Eom, S. H.; Kim, Y. M.; Kim, S. K. Marine bacteria: potential sources for compounds to overcome antibiotic resistance. *Appl Microbiol Biotechnol* 2013, 97, 4763-4773, doi:10.1007/s00253-013-4905-y.

16. Awad, H.; El-Shahed, K.; Aziz, R.; Sarmidi, M.; El Enshasy, H. Antibiotics as Microbial Secondary Metabolites: Production and Application. *Journal Tekologi* 2012, 59, 101-111, doi:10.11113/jt.v59.1593.

17. Garrigues, S.; Gandia, M.; Castillo, L.; Coca, M.; Marx, F.; Marcos, J. F.; Manzanares, P. Three Antifungal Proteins From *Penicillium expansum*: Different Patterns of Production and Antifungal Activity. *Frontiers in Microbiology* 2018, 9, doi: 10.3389/fmicb 0.2018.02370.

18. Selitrennikoff, C. P. Antifungal proteins. *Appl Environ Microbiol* 2001, 67, 2883-2894, doi:10.1128/ AEM.67.7.2883-2894.2001.

19. Messer, W. The bacterial replication initiator DnaA. DnaA and oriC, the bacterial mode to initiate DNA replication. *FEMS Microbiol Rev* 2002, 26, 355-374, doi:10.1111/j.1574-6976.2002.tb00620.x.

20. Jakimowicz, D.; Majka, J.; Messer, W.; Speck, C.; Fernandez, M.; Cruz Martin, M.; Sanchez, J.; Schauwecker, F.; Keller, U.; Schrempf, H.; et al. Structural elements of the *Streptomyces* oriC region and their interactions with the DnaA protein. *Microbiology (Reading)* 1998, 144 (Pt 5), 1281-1290, doi:10.1099/00221287-144-5-1281.

21. Rajewska, M.; Wegrzyn, K.; Konieczny, I. AT-rich region and repeated sequences—the essential elements of replication origins of bacterial replicons. *FEMS Microbiol Rev* 2012, 36, 408-434, doi:10.1111/j.1574-6976.2011.00300.x.

22. Yoon, S. H.; Ha, S. M.; Lim, J.; Kwon, S.; Chun, J. A large-scale evaluation of algorithms to calculate average nucleotide identity. *Antonie Van Leeuwenhoek* 2017, 110, 1281-1286, doi:10.1007/s10482-017-0844-4.

23. Blin, K.; Shaw, S.; Kloosterman, A. M.; Charlop-Powers, Z.; van Wezel, G. P.; Medema, M. H.; Weber, T. antiSMASH 6.0: improving cluster detection and comparison capabilities. *Nucleic Acids Res* 2021, 49, W29-W35, doi:10.1093/nar/gkab335.

24. Al-Askar, A.; M, A.; Rashad, Y. In vitro antifungal activity of *Streptomyces spororaveus* RDS28 against some phytopathogenic fungi. *African journal of agricultural research* 2011, 6, 2835-2842.

25. Frank, J. A.; Reich, C. I.; Sharma, S.; Weisbaum, J. S.; Wilson, B. A.; Olsen, G. J. Critical evaluation of two primers commonly used for amplification of bacterial 16S rRNA genes. *Appl Environ Microbiol* 2008, 74, 2461-2470, doi:10.1128/AEM.02272-07.

26. Boratyn, G. M.; Thierry-Mieg, J.; Thierry-Mieg, D.; Busby, B.; Madden, T. L. Magic-BLAST, an accurate RNA-seq aligner for long and short reads. *BMC Bioinformatics* 2019, 20, 405, doi:10.1186/s12859-019-2996-x.

27. Tamura, K.; Stecher, G.; Kumar, S. MEGA11: Molecular Evolutionary Genetics Analysis Version 11. *Mol Biol Evol* 2021, 38, 3022-3027, doi:10.1093/molbev/msab120.

28. Edgar, R. C. MUSCLE: multiple sequence alignment with high accuracy and high throughput. *Nucleic Acids Res* 2004, 32, 1792-1797, doi:10.1093/nar/gkh340.

29. Kumar, P. S.; Raj, J. P.; Duraipandiyan, V.; Ignacimuthu, S. Antibacterial activity of some actinomycetes from Tamil Nadu, India. *Asian Pac J Trop Biomed* 2012, 2, 936-943, doi:10.1016/s2221-1691(13)60003-9.

30. Bhargav, H. S.; Shastri, S. D.; Poornav, S. P.; Darshan, K. M.; Nayak, M. M. Measurement of the Zone of Inhibition of an Antibiotic. In Proceedings of the 2016 IEEE 6th International Conference on Advanced Computing (IACC), 27-28 Feb. 2016, 2016; pp. 409-414.

31. Kumar, A. K. UV mutagenesis treatment for improved production of endoglucanase and β-glucosidase from newly isolated thermotolerant actinomycetes, *Streptomyces griseoaurantiacus. Bioresources and Bioprocessing* 2015, 2, 22, doi:10.1186/s40643-015-0052-x.

32. Kutchma, A. J.; Roberts, M. A.; Knaebel, D. B.; Crawford, D. L. Small-scale isolation of genomic DNA from *Streptomyces* mycelia or spores. *Biotechniques* 1998, 24, 452-456, doi:10.2144/98243st05.

33. Sullivan, M. J.; Petty, N. K.; Beatson, S. A. Easyfig: a genome comparison visualizer. *Bioinformatics* 2011, 27, 1009-1010, doi:10.1093/bioinformatics/btr039.

34. Bos, J. D.; Meinardi, M. M. The 500 Dalton rule for the skin penetration of chemical compounds and drugs. *Exp Dermatol* 2000, 9, 165-169, doi:10.1034/j 0.1600-0625.2000.009003165.x.

SEQUENCE LISTING

The patent contains a lengthy sequence listing. A copy of the sequence listing is available in electronic form from the USPTO web site (https://seqdata.uspto.gov/docdetail?docId=US12661367B2). An electronic copy of the sequence listing will also be available from the USPTO upon request and payment of the fee set forth in 37 CFR 1.19(b)(3).

What is claimed is:

1. A *Streptomyces spororaveus* strain SC263 deposited with the German Collection of Microorganisms and Cell Cultures (DSMZ) under accession number DSM 34277.

2. A composition comprising the strain SC263 of claim 1.

3. The composition of claim 2, wherein the *Streptomyces spororaveus* strain SC263 is viable.

4. The composition of claim 2, wherein the *Streptomyces spororaveus* strain SC263 is inactivated.

5. An antibiotic produced by the strain SC263 of claim 1.

6. The antibiotic of claim 5, wherein the antibiotic exhibits an apparent molecular weight of larger than 5 kDa measured by membrane-filtration concentration.

7. The antibiotic of claim 5, wherein the antibiotic exhibits an apparent molecular weight of 10 kDa to 100 kDa, measured by membrane-filtration concentration.

8. The antibiotic of claim 5, wherein the antibiotic is effective against fungi.

9. The antibiotic of claim 5, wherein the antibiotic is effective against Gram-positive bacteria.

10. An antimicrobial composition or pharmaceutical composition comprising the antibiotic of claim 5 and a pharmaceutically acceptable carrier.

11. An antimicrobial composition or pharmaceutical composition comprising the strain SC263 of claim 1, and a pharmaceutically acceptable carrier.

12. The composition or pharmaceutical composition of claim 10, which is effective for treatment of a fungal infection.

13. The composition or pharmaceutical composition of claim 10, which is effective for treatment of a bacterial infection.

14. The composition or pharmaceutical composition of claim 11, which is effective for treatment of a fungal infection.

15. The composition or pharmaceutical composition of claim 11, which is effective for treatment of a bacterial infection.

16. The composition or pharmaceutical composition of claim 13, which is effective against Gram-positive bacteria.

17. The composition or pharmaceutical composition of claim 15, which is effective against Gram-positive bacteria.

18. The composition or pharmaceutical composition of claim 10, which is administered topically.

19. The composition or pharmaceutical composition of claim 11, which is administered topically.

\*    \*    \*    \*    \*